United States Patent [19]

Saunders et al.

[11] Patent Number: 5,166,364

[45] Date of Patent: Nov. 24, 1992

[54] MEVINIC ACID DERIVATIVES USEFUL AS ANTIHYPERCHOLESTEROLEMIC AGENTS AND METHOD FOR PREPARING SAME

[75] Inventors: Jeffrey O. Saunders, Holland, Pa.; Eric M. Gordon, Pennington, N.J.

[73] Assignee: E. R. Squibb & Sons, Inc., Princeton, N.J.

[21] Appl. No.: 765,806

[22] Filed: Sep. 26, 1991

Related U.S. Application Data

[60] Division of Ser. No. 662,597, Mar. 1, 1991, Pat. No. 5,099,035, which is a continuation of Ser. No. 431,263, Nov. 3, 1989, abandoned, which is a division of Ser. No. 316,203, Feb. 27, 1989, abandoned.

[51] Int. Cl.$^5$ .................... C07F 7/02; C07D 309/30
[52] U.S. Cl. .................... 549/214; 549/292
[58] Field of Search .................... 549/292, 214

[56] References Cited

U.S. PATENT DOCUMENTS

| | | | |
|---|---|---|---|
| 4,231,938 | 11/1980 | Monaghan et al. | 260/345.5 |
| 4,346,227 | 8/1982 | Terahara et al. | 560/119 |
| 4,444,784 | 4/1984 | Hoffman et al. | 549/292 |
| 4,448,979 | 5/1984 | Terhara et al. | 549/292 |
| 4,450,171 | 5/1984 | Hoffman et al. | 549/292 |
| 4,581,345 | 4/1986 | Wyvratt et al. | 514/30 |
| 4,582,915 | 4/1986 | Sleteinger et al. | 549/292 |
| 4,611,067 | 9/1986 | Volante et al. | 549/292 |
| 4,733,003 | 3/1988 | Ide et al. | 560/119 |
| 4,845,237 | 7/1989 | Decamp et al. | 549/214 |

FOREIGN PATENT DOCUMENTS 0065835 12/1982 European Pat. Off.
0142146 5/1985 European Pat. Off.

Primary Examiner—C. Warren Ivy
Assistant Examiner—Ba K. Trinh
Attorney, Agent, or Firm—Burton Rodney

[57] ABSTRACT

Mevinic acid derivatives are provided which are 6-hydroxy-8-(2,2-dimethyl-1-oxybutoxy-2-methyl)-substituted-decahydronaphthalene esters and have the structure

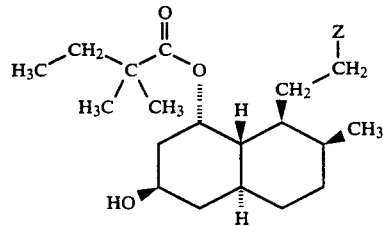

wherein Z is

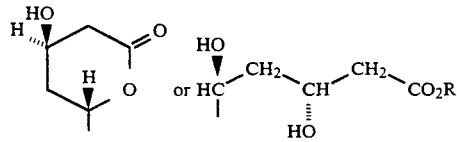

wherein R is alkali metal such as Na, or H or lower alkyl, and are HMG CoA reductase inhibitors and thus are useful as antihypercholesterolemic agents and in treating atherosclerosis, and also as antifungal agents.

In addition, a method for preparing the above-mevinic acid derivatives is also provided.

4 Claims, No Drawings

MEVINIC ACID DERIVATIVES USEFUL AS ANTIHYPERCHOLESTEROLEMIC AGENTS AND METHOD FOR PREPARING SAME

This is a division of application Ser. No. 662,597, filed Mar. 1, 1991, now U.S. Pat. No. 5,099,035, which is a continuation of application Ser. No. 431,263, filed Nov. 3, 1989, now abandoned, which is a division of application Ser. No. 316,203 filed Feb. 27, 1989, now abandoned.

FIELD OF THE INVENTION

The present invention relates to mevinic acid derivatives which are 6-hydroxy-8-(2,2-dimethyl-1-oxybutoxy-2-methyl)-substituted-decahydronaphthalene esters which are HMG CoA reductase inhibitors and thus are useful as antihypercholesterolemic agents and to a method for preparing such compounds.

BACKGROUND OF THE INVENTION

F. M. Singer et al., "New Inhibitors of in vitro Conversion of Acetate and Mevalonate to Cholesterol", *Proc. Soc. Exper. Biol. Med.*, 102, 370 (1959) and F. H. Hulcher, "Inhibition of Hepatic Cholesterol Biosynthesis by 3,5-Dihydroxy-3,4,4,-trimethylvaleric Acid and its Site of Action," *Arch. Biochem. Biophys.*, 146, 422 (1971) disclose that certain mevalonate derivatives inhibit the biosynthesis of cholesterol.

Singer et al. reported that fluoromevalonic acid is more effective in inhibiting biosynthesis of cholesterol (as measured by in vitro conversion of labeled acetate and labeled mevalonate into cholesterol) than Δ4-androstene-17α-ol-3-one-17β-oic acid and Δ1-testololactone.

Hulcher reported that an analog of mevalonic acid, namely, 3,5-dihydroxy-3,4,4-trimethylvaleric acid strongly inhibits cholesterol biosynthesis by rat liver homogenates.

U.S. Pat. No. 3,983,140 to Endo et al. discloses the fermentation product ML-236B referred to generically as compactin

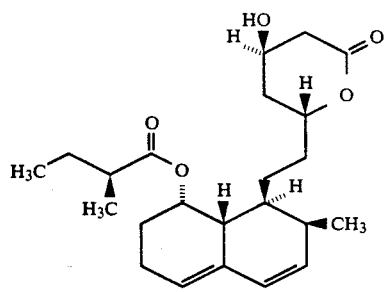

(also referred to as mevastatin) which is prepared by cultivation of a microorganism of the genus Penicillium. This fermentation process is disclosed in U.S. Pat. No. 4,049,495 issued Sep. 20, 1977 to Endo et al.

Brown, A. G., et al., (Beecham Pharmaceuticals Research Div.), "Crystal and Molecular Structure of Compactin, a New Antifungal Metabolite from Penicillium Brevicompactum", *J. Chem. Soc. Perkin I.* 1165-1170 (1976) confirms that compactin has a complex mevalonolactone structure as disclosed by Endo et al. in the above patents.

U.S. Pat. No. 4,231,938 to Monaghan et al. discloses mevinolin (lovastatin, Monacolin K)

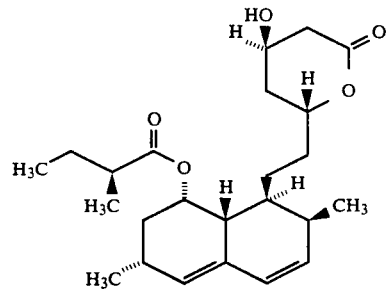

(also referred to as MK-803) which is prepared by culturing a microorganism of the genus Aspergillus.

U.S. Pat. No. 4,346,227 to Terahara et al discloses pravastatin

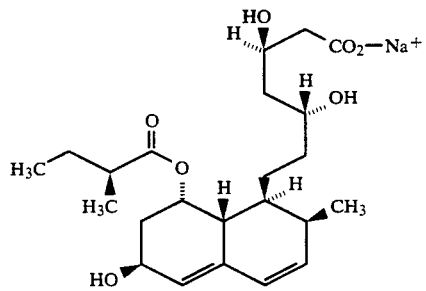

Pravastatin is prepared by the enzymatic hydroxylation of compactin or its carboxylic acid as disclosed in U.S. Pat. No. 4,410,629 to Terahara et al.

U.S. Pat. No. 4,448,979 issued May 15, 1984 to Terahara et al discloses the lactone of pravastatin.

U.S. Pat. Nos. 4,444,784 and 4,450,171 to Hoffman et al disclose various antihypercholesolemic compounds including synvinolin (simvastatin)

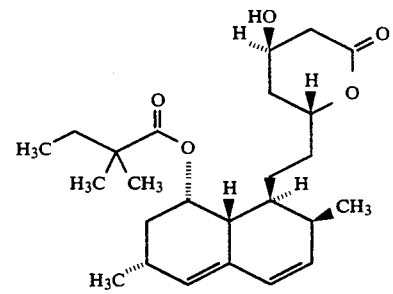

as well as compounds of the structures

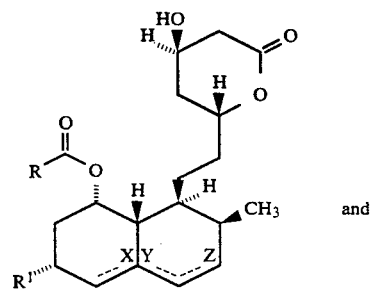

and

-continued

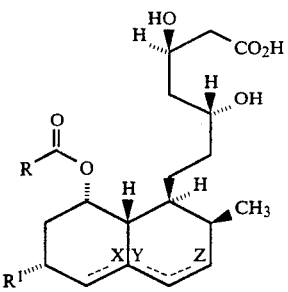

wherein $R^1$ is H or $CH_3$, R can be an alkyl group including

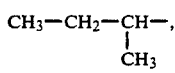

X, Y and Z are single and/or double bonds in all possible combinations.

European Patent Application 0065835A1 filed by Sankyo discloses cholesterol biosynthesis inhibiting compounds of the structure

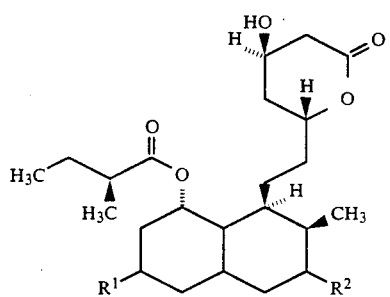

and their corresponding free carboyxlic acids, which may be represented by the following formula

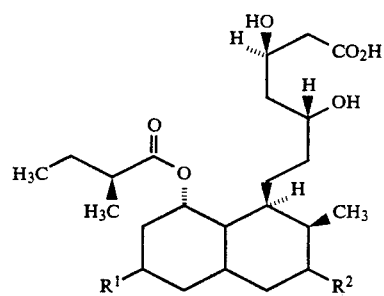

(in which one of $R^1$ and $R^2$ represents a hydrogen atom and the other represents a hydroxy group), and salts and esters of the carboxylic acids.

European Patent Application 0142146A2 filed by Merck discloses mevinolin-like compounds of the structure

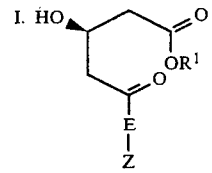

wherein
$R^1$ is
1) hydrogen,
2) $C_{1-4}$alkyl,
3) 2,3-dihydroxypropyl,
4) alkali metal cation, such as $Na^+$, or $K^+$, or
5) ammonium of formula $N^+R^3R^4R^5R^6$ wherein $R^3$, $R^4$, $R^5$ and $R^6$ are independently hydrogen or $C_{1-4}$alkyl or two of $R^3$, $R^4$, $R^5$ and $R^6$ are joined together to form a 5 or 6-membered heterocycle such as pyrrolidino or piperidino with the nitrogen to which they are attached;
E is $-CH_2CH_2-$, $-CH=CH-$, or $-(CH_2)_3-$;
and Z is

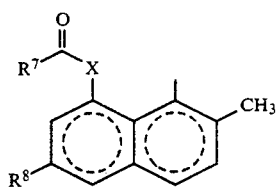

wherein the dotted lines represent all of the possible oxidation states of the bicyclic system such as naphthalene, dihydro-, tetrahydro-, hexahydro-, octahydro- and decahydronaphthalene;
X is $-O-$ or

wherein
$R^9$ is H or $C_{1-3}$alkyl;
$R^7$ is $C_{2-8}$alkyl; and
$R^8$ is H or $-CH_3$;

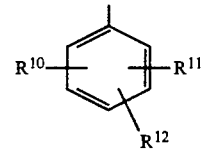

wherein $R^{10}$, $R^{11}$ and $R^{12}$ are independently
a) hydrogen,
b) halogen, such as bromo, chloro or fluoro,
c) $C_{1-4}$alkyl,
d) halo-$C_{1-4}$alkyl,
e) phenyl either unsubstituted or substituted with one or more of
  i) $C_{1-4}$alkyl,
  ii) $C_{1-4}$alkyl,
  iii) $C_{2-8}$alkanoyloxy, or
  iv) halo-$C_{1-4}$alkyl, v) halo, such as bromo, chloro or fluoro,
f) OR$^{13}$ wherein R$^{13}$ is
  i) hydrogen,
  ii) C$_{1-8}$alkanoyl,
  iii) benzoyl,
  iv) phenyl,
  v) halophenyl,
  vi) phenyl-C$_{1-3}$alkyl, either unsubstituted or substituted with one or more halogen, C$_{1-4}$alkoxy, C$_{1-4}$alkyl or halo-C$_{1-4}$alkyl,
  vii) C$_{1-9}$alkyl,
  viii) cinnamyl,
  ix) halo-C$_{1-4}$alkyl,
  x) allyl,
  xi) C$_{3-6}$cycloalkyl-C$_{1-3}$alkyl,
  xii) adamantyl-C$_{1-3}$alkyl,

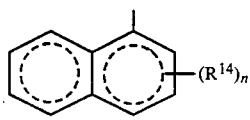

3)

wherein n is 0–2, and R$^{14}$ is halo such as chloro, bromo or fluoro, or C$_{1-4}$ alkyl, and

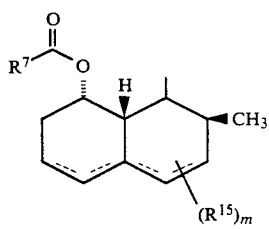

4)

wherein the dotted lines represent possible double bonds there being 0, 1 or 2 double bonds; m represents 1, 2 or 3; and R$^{15}$ is
1) methyl,
2) hydroxy,
3) C$_{1-4}$alkoxy,
4) oxo or
5) halo.

In the discussion of the prior art at pages 2 and 3 of the above European patent, it is indicated that HMG CoA reductase inhibitors reported in the patent literature and elsewhere include compactin; mevinolin, di- and tetrahydro derivatives thereof; analogs with different esters in the 8-position of the polyhydronaphthalene moiety, totally synthetic analogs, wherein the polyhydronaphthalene moiety is replaced by substituted mono- and bicyclic aromatics. The applicant states at pages 3 and 4 as follows:

"But in all instances the active compound included a 4-hydroxytetrahydropyran-2-one ring or the corresponding 3,5-dihydroxy acid, or derivaties thereof, formed by opening the pyranone ring such as:

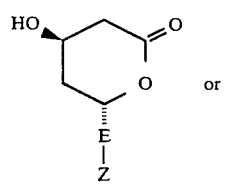

4-hydroxytetrahydropyran-2-one

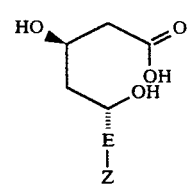

3,5,-dihydroxy-acid

In all of these compounds the 3,5-dihydroxy acid or corresponding lactone moiety is present and the particular stereochemistry depicted is essential for manifestation of the optimum enzyme inhibitory activity.

With the present invention there are provided compounds structurally related to those lactones and dihydroxy acids that do not have the 5-hydroxy functionality, do not form a lactone ring, and are incapable of stereochemical variation at the 5-position of the acid because the 5-carbon is not asymmetric. On the contrary, the 5-carbon carries an oxo function which greatly facilitates the total synthesis of active compounds in that by eliminating one asymmetric center it is unnecessary to separate diastereoisomers or to conduct a stereoselective synthesis to obtain optimum enzyme inhibitory activity. It is believed that structures I are reduced in situ to generate the "active" inhibitors of structure II or IIa."

DESCRIPTION OF THE INVENTION

In accordance with the present invention, compounds are provided having the structure

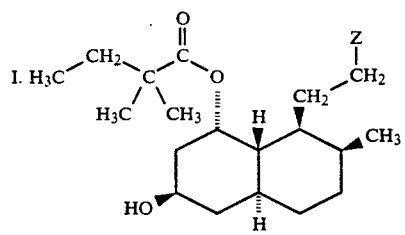

wherein Z is

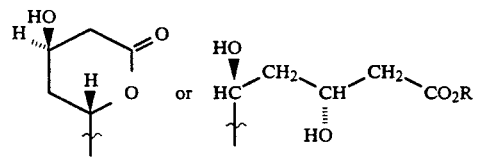

wherein R is alkali metal such as Na, K or Li, lower alkyl of 1 to 7 carbons or H. The above compounds will be in substantially pure form.

Preferred are compounds of structure I wherein Z is

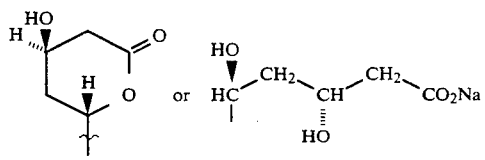

In addition, in accordance with the present invention, a method is provided for preparing the compounds of structure I in substantially pure form, which method includes the steps of providing a lactone of the structure

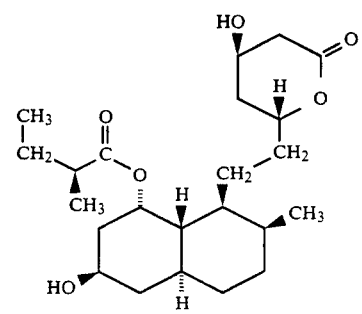

hydrolyzing lactone A by treating A with a strong aqueous base and then acid to form the corresponding tetrahydroxy acid of the structure B;

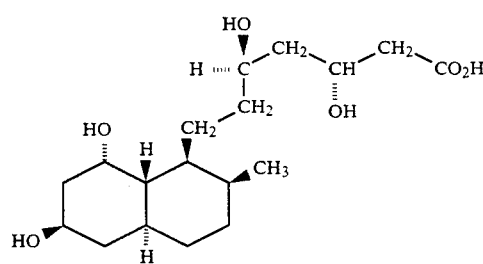

subjecting the resulting tetrahydroxy acid to relactonization by treating with trifluoroacetic acid to form triol II which is a novel intermediate;

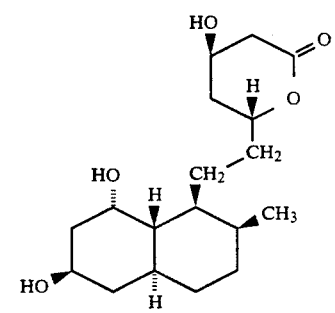

subjecting triol II to selective silylation by treating with a silyl chloride protecting agent (Pro-Cl) in the presence of an amine base to form the bis-silyl ether III which is a novel intermediate;

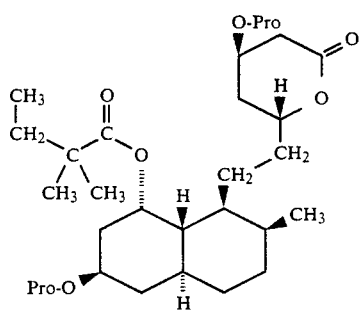

(wherein Pro represents a silyl protecting group)

acylating bis-silyl ether III by reacting same with 2,2-dimethylbutyryl chloride in the presence of appropriate catalyst such as dimethylaminopyridine and pyridine to form the bis-silyl ether IV which is a novel intermediate;

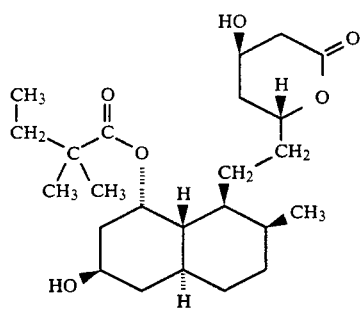

and subjecting IV to desilylation by treating IV with hydrofluoric acid-pyridine in the presence of an organic solvent such as acetonitrile to form a compound of formula IA of the invention wherein Z is in lactone form

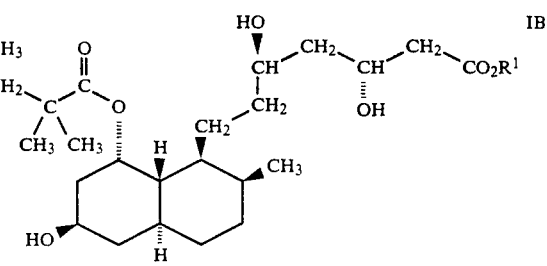

The formula IA compound of the invention may be hydrolyzed by treating IA with aqueous alkali metal base to form the compound IB of the invention

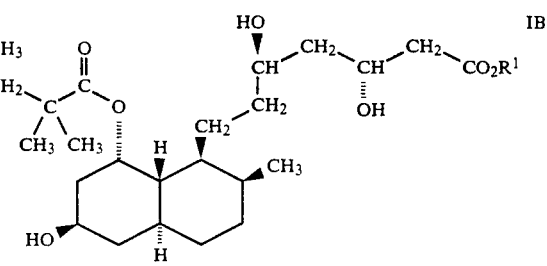

wherein R[1] is an alkali metal.

Compound IB may be converted to the corresponding acid by treating IB with mild aqueous acid such as potassium bisulfate to form compound of the invention IC

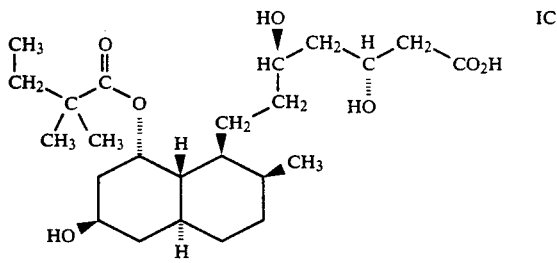

Compounds of the invention where R is lower alkyl may be prepared as follows.

Esters, preferably alkyl esters, of the carboxylic acids of formula IC may be obtained by contacting the carboxylic acid of formula IC with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction: suitable solvents include benzene, chloroform, ethers and the like. Alternatively, the desired product may be obtained by contacting the carboxylic acid of formula IC with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula IC with a halide, preferably an alkyl halide, in a suitable solvent: preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating.

DETAILED DESCRIPTION OF THE INVENTION

In carrying out the method of the invention for preparing compounds of formula IA, the lactone A is treated with a strong base such as an alkali metal hydroxide such as lithium hydroxide, sodium hydroxide or potassium hydroxide at a temperature within the range of from about 75° to about 125° C., preferably from about 100° to about 110° C., for a period of from about 2 to about 24 hours, and preferably from about 6 to about 8 hours and employing a molar ratio of base to lactone A of within the range of from about 2:1 to about 20:1 and preferably from about to 4:1 to about 6:1. The reaction mixture is then cooled to ambient temperature and brought to pH 2-3 with an acid such as KHSO$_4$(s), hydrochloric acid or sulfuric acid to form a tetrahydroxy acid. The tetrahydroxy acid is separated from the reaction mixture employing conventional procedures and is then dissolved in a suitable solvent such as ethyl acetate, tetrahydrofuran or acetonitrile and treated with trifluoroacetic acid, hydrofluoric acid or Amberlyst 15 ion exchange resin for a period of from about 4 to about 24 hours and preferably from about 6 to about 8 hours to form the triol II.

Triol II is slurried with, for example, methylene chloride or tetrahydrofuran, and then treated with amine base such as imidazole, triethylamine, ethyldiisopropylamine or N,N-dimethylaniline and then with a silyl chloride protecting agent such as tertiary-butyldimethylsilyl chloride, tertiary-butyldiphenylsilyl chloride, triethylsilyl chloride or phenyldimethylsilyl chloride for a period of from about 8 to about 24 hours, preferably from about 12 to about 16 hours, to form the novel bis-silyl ether intermediate III. In carrying out the above reaction the amine base is employed in a molar ratio to the triol II of within the range of from about 2:1 to about 4:1 and preferably from about 2.5:1 to about 3.5:1 and the silyl chloride protecting agent is employed in a molar ratio to triol II of within the range of from about 2:1 to about 4:1 and preferably from about 2.5:1 to about 3:1. The bis-silyl ether III is then acylated by reacting same with 2,2-dimethylbutyryl chloride in the presence of appropriate catalyst such as dimethylaminopyridine, and pyridine at a temperature within the range of from about 25° to about 100° C. and preferably from about 70° to about 80° C. to form the novel acylated bis-silyl ether intermediate IV. In carrying out the above acylation the 2,2-dimethylbutyryl chloride is employed in a molar ratio to ether III of within the range of from about 1:1 to about 10:1 and preferably from about 4:1 to about 6:1.

The ether IV is then deprotected by treating a solution of IV in a solvent such as acetonitrile or tetrahydrofuran with hydrofluoric acid-pyridine, hydrofluoric acid or tetrabutylammonium fluoride for a period of from about 5 to 60 minutes, to form compound IA of the invention.

Compound IB of the invention is obtained by hydrolyzing IA with aqueous base such as alkali metal hydroxide like sodium hydroxide, lithium hydroxide or potassium hydroxide in the presence of suitable solvent such as dioxane, acetonitrile or tetrahydrofuran.

The starting lactone A may be prepared as described in European Patent Application 0065835 (Sankyo).

Compound IC of the invention is obtained by careful acidification of an aqueous solution of compound IB with an acid such as aqueous potassium bisulfate followed by extraction of IC from the aqueous mixture with an organic solvent such as ethyl acetate, dichloromethane or chloroform. The organic extracts are then dried with MgSO$_4$ or Na$_2$SO$_4$, filtered and concentrated to provide IC.

Compounds of the invention of formula I where R is lower alkyl are obtained by adding to a solution of compound IA in an appropriate alcohol a slight molar excess of the corresponding alkoxide. The mixture is then diluted with an organic solvent such as ethyl acetate or chloroform and extracted with water. The organic portion is dried with MgSO$_4$ or Na$_2$SO$_4$, filtered and concentrated to provide lower alkyl ester of compounds of formula I.

Alternatively, compounds of the invention of formula I where R is lower alkyl are obtained by solvolysis of the lactone in the presence of an appropriate alcohol and an acid catalyst, which may be an inorganic acid such as hydrochloric acid or sulphuric acid, a Lewis acid such as boron trifluoride or an acidic ion-exchange resin. In the case of an inorganic acid or Lewis acid, isolation of the product ester involves neutralization and extraction followed by drying, filtering and comcentrating. In the case of an ion exchange resin, simple filtration and concentration will provide the product ester.

Alternatively, Compound IC of this invention may be treated as a solution in a suitable solvent, i.e. a solvent such as diethyl ether, tetrahydrofuran or dichloromethane that does not interfere with the reaction, with an appropriate diazoalkane. The product alkyl esters can then be isolated by concentration of the reaction mixture.

The compounds of formula I of the invention will be formulated with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations.

A typical capsule for oral administration contains active ingredients (25 mg), lactose (75 mg) and magnesium stearate (15 mg). The mixture is passed through a 60 mesh sieve and packed into a No. 1 gelatin capsule.

A typical injectable preparation is produced by asceptically placing 25 mg of a water soluble salt of sterile active ingredient into a vial, asceptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis and in treating nephrotic hyperlipidemia. In addition, the compounds of the invention increase plasma high density lipoprotein cholesterol levels.

As HMG CoA reductase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, DEAE-Sephadex as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors.

The above compounds to be employed in combination with the HMG CoA reductase inhibitor of the invention will be used in amounts as indicated in the Physicians' Desk Reference (PDR).

The inhibition of HMG CoA reductase using the compounds of the invention may be measured by the following tests.

The dose to be administered depends on the unitary dose, the symptoms, and the age and the body weight of the patient. A dose for adults is preferably between 20 and 2,000 mg per day, which can be administered in a single dose or in the form of individual doses from 1-4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities they are admixed with suitable formulating agents, powders, emulsifying agents or solvents such as aqueous ethanol and sprayed or dusted on the plants to be protected.

In addition, the compounds of the invention may be useful in elevating HDL-cholesterol while lowering levels of LDL-cholesterol and serum triglycerides, and for treating tumors.

The following working examples represent preferred embodiments of the invention. Unless otherwise specified, all temperature are in degrees Centigrade (°C.).

EXAMPLE 1

[1S-[1α,3β,4aα,7β,8β(2S*,4S*),8aβ]]-2,2-Dimethylbutanoic acid,
decahydro-3-hydroxy-7-methyl-8-[2-(tetrahydro-4-hydroxy-6-oxo-2H-pyran-2-yl)-ethyl]-1-naphthalenyl ester

A.
[1S-[1α(R*),3β,7β,8β(2S*,4S*),8aβ]]-2-Methylbutanoic acid,
1,2,3,7,8,8a-Hexahydro-3-hydroxy-7-methyl-8-[2-(tetrahydro-4-hydroxy-6-oxo-2H-pyran-2-yl)ethyl]-1-naphthalenyl ester

Method A(1)

Pravastatin (sodium salt) (2.001 g, 4.49 mmole) was partitioned between ethyl acetate-5% KHSO$_4$ (75 ml each). The organic phase was washed with saturated NaCl solution, dried over Na$_2$SO$_4$ and evaporated to dryness to give the free acid (1.888 g) as a colorless glass.

The free acid (1.888 g) was taken up in dry toluene (100 ml) and refluxed through a Soxelet containing 3 Å molecular sieves for three hours. The solution was evaporated to give 1.80 g of crude title compound as a white solid. The crude product was purified by flash chromatography on silica gel (100 g LPS-1), eluting with acetone-hexane (35:65) to give pure title diene-lactone (1.560 g, 86%) as a white crystalline solid, m.p. 143.5°-144.5° C. [α]$_D$=+199.7° (c=0.59, CHCl$_3$).

TLC: (CH$_3$OH—CH$_2$Cl$_2$; 1:9) Rf=0.28.

$^1$H-NMR (CDCl$_3$, 270 MHz)δ0.90 (t, 3H), 0.93 (d, 3H), 1.03 (d, 3H), 4,36 (broad s, 1H), 4,38 (broad m, 1H), 4.62 (broad m, 1H), 5.40 (broad s, 1H), 5.57 (broad s, 1H), 5.89 (dd, 1H), 6.01 (d, 1H).

Method A(2)

Pravastatin (sodium salt; 30.0 g, 67.2 mmole) was partitioned between 275 mL H$_2$O, containing 18.3 g (134 mmole) of KHSO$_4$, and 575 mL of ethyl acetate. The aqueous phase was extracted twice with 275 mL portions of ethyl acetate, all organics were combined, dried (MgSO$_4$) and concentrated in vacuo.

The free acid was redissolved in 900 mL of ethyl acetate and treated with 0.5 mL of trifluoroacetic acid at 0° C. The solution was brought immediately to ambient tempperature and stirred for 24 hours before treating with 3 mL of saturated NaHCO$_3$. The reaction mixture was then filtered and concentrated in vacuo to a white solid from which the pure lactone could be isolated via recrystallization (hot ethyl acetate-hexanes) in a yield of 24.45 g (90%).

B. [1S-[1α(R*),3β,7β,8β(2S*,4S*),3aβ]]-2-Methylbutanoic acid, 3-[[(1,1-dimethylethyl)-dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl ester A solution of 8.43 g (20.7 mmol, 100 eq.) of Part A diene-lactone in 80 ml of dry tetrahydrofuran (THF) under argon at ambient temperature was treated with 1.76 g (25.9 mmol, 1.25 eq.) of imidazole followed by 3.44 g (22.8 mmol, 1.10 eq.) of t-butyldimethylsilyl chloride (TBSCl). After stirring for 26 hours, the reaction mixture was diluted with 80 ml of diethyl ether, filtered and concentrated in vacuo. Purification of the residue by flash chromatography (Merck silica gel; 40% ethyl acetate/hexanes) gave 7.41 g (69% yield) of the monosilylated product as a white solid, mp 111°–115° C.

TLC: $R_f$(silica gel, 100% ethyl acetate)=0.47 (UV* and anisaldehyde stain)

IR (KBr): 775, 838, 891, 1017, 1044, 1075, 1156, 1166, 1183, 1255, 1376, 1462, 1726, 2857, 2883, 2930, 2957, 3420, 3429, 3439 cm$^{-1}$.

$^1$H NMR (270 MHz; CDCl$_3$; referenced with CHCl$_3$@7.24 ppm)

| δ | | |
|---|---|---|
| 5.93–5.96 | (d, 1H, J=9.50 Hz) | |
| 5.78–5.84 | (dd, 1H, J=9.5, 5.8 Hz) | |
| 5.44 | (m, 1H) | |
| 5.34 | (m, 1H) | |
| 4.39–4.40 | (m, 1H) | |
| 4.30–4.32 | (m, 1H) | |
| 2.50–2.65 | (ABX, 2H) | |
| 2.28–2.38 | (m, 5H) | |
| 1.67–2.00 | (m, 2H) | |
| 1.55–1.66 | (m, 4H) | |
| 1.19–1.45 | (m, 4H) | |
| 1.07–1.09 | (d, 3H, J=6.86 Hz) | |
| 0.83–0.88 | (m, 6H, J=4.75 Hz) | |
| 0.85 | (s, 9H) | |
| 0.03 | (s, 3H) | |
| 0.02 | (s, 3H) | |
| $^{13}$C NMR(67.8MHz, CDCl$_3$): | δ | −4.73, −4.67, 11.83, 13.62, 17.02, 18.23, 23.70, 25, 86, 26.66, 30.95, 32, 80, 36.11, 36.66, 37.46, 38, 61, 41.75, 62.60, 65.54, 69.51, 76.11, 127.16, 127.62, 134.45, 135.14, 170.27, 176.41. |
| Mass Spec. (NH$_3$ Dep.): | | m/e 520(M+) |

C. [1S-[1α(R*), 3β, 4aα, 7β, 8β, (2S*, 4S*), 8aβ]]-2-Methylbutanoic acid, 3-[[(1,1-dimethylethyl)-dimethylsilyl]oxy]decahydro-7-methyl-8-[2-(tetrahydro-4-hydroxy-6-oxo-2H-pyran-2-yl)-ethyl]-1-naphthalenyl ester To a degassed, argon purged solution of 9.38 g (18.0 mmol) of Part B mono-silylated product in 200 ml of ethyl acetate was added 1.4 g of 10% Pt-C. This suspension was subjected to 50 psi of H$_2$ in a Parr hydrogenation apparatus for 14.5 hours. The filtered reaction mixture was concentrated and products isolated by flash chromatography. Elution with 45% hexanes in ethyl acetate gave 7.73 g (82%) of the title compound as a clear glass and elution with 30% hexanes in ethyl acetate gave 0.98 g (13%) hydrogenated, desilyated product (Part D compound).

TLC: Rf=0.45 (silica gel, 100% ethyl acetate, anisaldehyde stain)

IR (CH$_2$Cl$_2$-film): 398.4, 774.6, 836.1, 873.8, 1074.1, 1099.4, 1128.7, 1153.6, 1171.3, 1185.2, 1252.5, 1381.4, 1460.2, 1727.9, 2855.1, 2879.3, 2926.3, 2956.0 cm$^{-1}$ $^1$H NMR (270 MHz; CDCl$_3$; Referenced with CHCl$_3$@7.24 ppm)

| δ | | |
|---|---|---|
| 5.19–5.21 | (m, 1H) | |
| 4.55–4.60 | (m, 1H) | |
| 4.27–4.38 | (m, 1H) | |
| 3.91–4.03 | (m, 1H) | |
| 2.52–2.72 | (ABX, 2H) | |
| 2.22–2.36 | (m, 1H) | |
| 1.85–2.00 | (m, 3H) | |
| 1.72–1.84 | (br d, 1H) | |
| 1.51–1.72 | (m, 9H) | |
| 1.36–1.50 | (m, 9H) | |
| 1.09–1.12 | (d, 3H, J=7.38Hz) | |
| 0.84–0.89 | (t, 2H, J=7.38Hz) | |
| 0.83 | (s, 9H) | |
| 0.77–0.80 | (d, 3H, J=6.86Hz) | |
| −0.006 | (s, 3H) | |
| −0.010 | (s, 3H) | |
| $^{13}$C NMR (67.8MHz, CDCl$_3$): | δ | −4.73, −4.67, 11.80, 17.07, 18.14, 24.65, 25.83, 26.72, 28.02, 28.85, 32.71, 33.00, 35.65, 36.11, 38.61, 39.68, 40.34, 41.84, 43.11, 43.39, 62.66, 66.75, 70.32, 76.37, 170.33, 175.97 |
| Mass Spec. (Dep NH$_3$): | | m/e 525 (M + H)$^+$ |

D. [1S-[1α(R*),3β,4aα,7β,8β(2S*,4S*),8aβ]]-2-Methylbutanoic acid, decahydro-3-hydroxy-7-methyl-8-[2-(tetrahydro-4-hydroxy-6-oxo-2H-pyran-2-yl)ethyl]-1-naphthalenyl ester To a solution of 18.5 g (35.3 mmol) of Part C compound in 200 mL of CH$_3$CN at 0° C. was added 22 mL of HF-pyridine. Following a 30 minute reaction period, the mixture was diluted with 500 mL of ethyl acetate and washed sequentially with saturated CuSO$_4$ (aqueous, 100 mL), brine (2×50 mL), saturated NaHCO$_3$ (aqueous, 2×50 ml) and brine (1×50 mL). The organic solution was dried (MgSO$_4$) and concentrated in vacuo to yield a white solid from which pure product was isolated via recrystallization (hot ethyl acetate and hexanes) in a yield of 13.1 g (90%), m.p. 156°–157° C.

TLC: R$_f$=0.28 (Silica gel; CH$_3$OH/CH$_2$Cl$_2$ 1:9)

$^1$H NMR (270 MHz; CDCl$_3$ with CHCl$_3$@7.24 ppm)δ5.16 (br s, 1H), 4.48 (br m, 1H), 4.19 (sextet, 1H, CHOH), 3.69 (br m, 1H, CH—OH), 3.38 (d, 1H, OH), 2.77 (d, 1H, OH), 1.12 (d, 3H), 0.89 (t, 3H), 0.82 (d, 3H) ppm.

E. [1S-[1α,3β,4aα,7β,8β(2S*,4S*),8aβ]]-Decahydro-7-methyl-8-[2-(tetrahydro-4-hydroxy-6-oxo-2H-pyran-2-yl)ethyl]-1,3-naphthalendiol A mixture of 3.0 g (7.31 mmol, 1.0 eq.) of Example 1, Part D compound and 4.0 g (95.3 mmol, 13 eq.) of LiOH.H$_2$O in 20 ml of H$_2$O were brought to reflux for a period of 16 hours before cooling to ambient temperature and acidifying with excess KHSO$_4$(s). The tetrahydroxy-acid was exhaustively extracted with ethyl acetate and the extracts were dried (Na$_2$SO$_4$) and concentrated to an oil in vacuo.

The oil was then redissolved in 25 ml of ethyl acetate and treated with 250 μl of trifluoroacetic acid and stirred at ambient temperature for 18 hours. The pure title lactone was then isolated by filtration of the reaction mixture in a yield of 1.62 g (68%).

TLC: R$_f$=0.36 (Silica gel; 8:1:1 CH$_2$Cl$_2$/CH$_3$OH/acetic acid)

$^1$H NMR (270 MHz; CD$_3$OD; Referenced with CH$_3$OH@3.30 ppm)

| δ | 4.64–4.69 | (m, 1H) |
|---|---|---|
|   | 4.22–4.25 | (m, 1H) |
|   | 4.13–4.14 | (m, 1H) |
|   | 3.28–3.30 | (m, 1H) |
|   | 2.45–2.75 | (ABX, 2H) |
|   | 2.05–2.17 | (d, 1H) |
|   | 1.60–2.05 | (m, 6H) |
|   | 1.20–1.60 | (m, 9H) |
|   | 0.90–1.05 | (m, 2H) |
|   | 0.82–0.85 | (d, 3H, J=6.86Hz) |

F.
[1S-[1α,3β,4aα,7β,8β(2S*,4S*),8aβ]]-3-[[(1,1-Dimethylethyl)dimethylsilyl]oxy]-8-[2-[[[(1,1-dimethylethyl)-dimethylsilyl]oxy]-tetrahydro-6-oxo-2H-pyran-2-yl]ethyl]-decahydro-7-methyl-1-naphthalenol To a slurry of 1.62 g (4.96 mmol, 1.0 eq) of Part E triol in 40 ml of dry CH$_2$Cl$_2$ was added 3.38 g (49.6 mmol, 10.0 eq) of imidazole and 3.28 g (21.8 mmol, 4.4 eq) of TBSCl and the mixture was stirred at ambient temperature for 18 hours. The reaction mixture was then diluted with 25 mL diethyl ether, filtered and concentrated in vacuo. The purified title bis-silyl ether was isolated by silica gel chromatography (25% ethyl acetate in hexanes) in a yield of 2.70 g (98.2%).

TLC R$_f$=0.72 (Silica gel; ethyl acetate)

$^1$H NMR (270 MHz; CDCl$_3$; Referenced with CHCl$_3$@7.24 ppm)

| δ | 4.63–4.68 | (m, 1H) |
|---|---|---|
|   | 4.25–4.27 | (m, 1H) |
|   | 4.15 | (br s, 1H) |
|   | 3.91–4.00 | (m, 1H) |
|   | 2.53–2.56 | (ABX, 2H) |
|   | 2.02–2.07 | (m, 1H) |
|   | 1.92–1.94 | (m, 1H) |
|   | 1.61–1.79 | (m, 4H) |
|   | 1.21–1.52 | (m, 7H) |
|   | 0.95–1.10 | (m, 2H) |
|   | 0.84–0.89 | (t, 2H, J=6.07Hz) |
|   | 0.85 | (s, 18H) |
|   | 0.78–0.80 | (d, 3H, J=6.86Hz) |
|   | 0.47 | (s, 3H) |
|   | 0.39 | (s, 3H) |
|   | 0.03 | (s, 6H) |

G.
[1S-[1α(R*),3β,7β,8β(2S*,4S*),8aβ]]-2-Methylbutanoic acid, 3-[[(1,1-dimethylethyl)-dimethylsilyl]oxy]-8-[2-[[[(1,1-dimethylethyl)dimethylsilyl]oxy]tetrahydro-6-oxo-2H-pyran-2-yl]ethyl]decahydro-7-methyl-1-naphthalenyl ester To a solution of 2.7 g (4.86 mmol, 1.0 eq) of Part F alcohol in 20 ml of dry pyridine was added 610 mg (5.0 mmol, 1.01 eq) of 4-dimethylaminopyridine (DMAP) followed by 3.3 g (24.3 mmol, 5 eq) of 2,2-dimethylbutyryl chloride in a dropwise fashion with vigorous stirring. The mixture was heated to 75° C. for 18 hours before cooling to ambient temperature and filtering with an ethyl acetate rinse. The filtrate was concentrated in vacuo and the pure title product isolated by elution from silica gel (7% ethyl acetate in hexanes) in a yield of 1.93 g (60.8%).

TLC R$_f$=0.752 (Silica gel; 25% ethyl acetate in hexanes)

$^1$H NMR (270 MHz; CDCl$_3$; Referenced with CHCl$_3$@7.24 ppm)

| δ | 5.15–5.27 | (m, 1H) |
|---|---|---|
|   | 4.48–4.60 | (m, 1H) |
|   | 4.23–4.26 | (m, 1H) |
|   | 3.62–3.84 | (m, 1H) |
|   | 2.47–2.63 | (ABX, 2H) |
|   | 2.06–2.17 | (br d, 1H) |
|   | 1.86–1.98 | (m, 1H) |
|   | 1.70–1.85 | (m, 2H) |
|   | 1.05–1.62 | (m, 14H) |
|   | 1.51–1.58 | (q, 2H, J=6.86Hz) |
|   | 1.12 | (s, 6H) |
|   | 0.82–0.86 | (t, 3H, J=5.80Hz) |
|   | 0.85 | (s, 9H) |
|   | 0.83 | (s, 9H) |
|   | 0.77–0.82 | (d, 2H, J=6.86Hz) |
|   | 0.05 | (s, 6H) |
|   | −0.01 | (s, 3H) |
|   | −0.02 | (s, 3H) |

H.
[1S-[1α,3β,4aα,7β,8β(2S*,4S*),8aβ]]-2,2-Dimethylbutanoic acid, decahydro-3-hydroxy-7-methyl-8-[2-(tetrahydro-4-hydroxy-6-oxo-2H-pyran-2-yl)ethyl]-1-naphthalenyl ester To a solution of 1.93 g (3.25 mmol) of Part G bis-silyl ether in 20 ml of CH$_3$CN was added 1 ml of HF-pyridine at ambient temperature. Following a 15 minute reaction period, the mixture was diluted with 50 ml of ethyl acetate, washed twice with brine and concentrated in vacuo. Pure title compound was isolated as a white crystalline material by crystallization from hot ethyl acetate/hexanes in a yield of 964 mg (69.9%), (mp 196.5°–198.0° C.).

TLC: R$_f$=0.41 (Silica gel; 25% ethyl acetate in hexanes)

$^1$H NMR (270MHz, CDCl$_3$, Referenced with CHCl$_3$@7.24 ppm)

| δ | 5.22–5.26 | (m, 1H) |
|---|---|---|
|   | 4.52–4.58 | (m, 1H) |
|   | 4.31–4.35 | (m, 1H) |
|   | 3.78–3.82 | (m, 1H) |
|   | 2.53–2.75 | (ABX, 2H) |
|   | 2.18–2.26 | (ddd, 1H) |
|   | 2.06–2.07 | (d, 1H, J=3.17Hz) |
|   | 1.87–2.06 | (br d, 2H) |
|   | 1.80–1.85 | (m, 1H) |
|   | 1.00–1.70 | (m, 16H) |
|   | 1.13 | (s, 6H) |
|   | 0.80–0.87 | (t, 2H, J=7.65Hz) |
|   | 0.79–0.82 | (d, 3H, J=6.86Hz) |

$^{13}$C NMR (67.8 MHz,CDCl$_3$, Referenced with CDCl$_3$@77.00 ppm) δ177.36, 170.56, 76.40, 70.03, 66.17, 62.43, 43.30, 43.19, 43.11, 42.96, 39.77, 38.53, 36.08, 35,68, 33.17, 32.97, 32.62, 28.79, 27.93, 24.82, 24.65, 11.72, 9.30 ppm.

IR: (CHCl$_3$ Solution): 3013.79, 2965.38, 2930.43, 2876.47, 1715.53, 1636.16, 1469.96, 1461.2, 1382.34, 1241.78, 1205.69, 1156.37, 1030.79

Mass Spec.: (CI; DEP; CH$_4$/NO$_2$) (M+H)$^+$@425.

Elemental Analysis (%)

Calcd. for 0.35 moles of H₂O
(Effective M.W.=430.89)

|   | Calc. | Found |
|---|-------|-------|
| C | 66.91 | 66.90 |
| H | 9.52  | 9.53  |

$[\alpha]_D = +68.5°$ (c=0.20, CH₂Cl₂)

EXAMPLE 2

[1S-[1α(βS*,<dS*),2α,4aβ,6α,8β,8aα]]-Decahydro-<b,<d,6-trihydroxy-2-methyl-8-(2,2-dimethyl-1-oxobutoxy)-1-naphthaleneheptanoic acid, monosodium salt To a solution of 1.06 g (2.50 mmol, 1.0 eq) of Example 1 lactone in 20 ml of dioxane was added 2.75 ml (2.75 mmol, 1.1 eq) of 1N NaOH in a dropwise fashion. After 35 minutes, the reaction was concentrated to a volume of ca. 3 ml and the purified product isolated, after elution from CHP-20P (H₂O followed by 25% CH₃CN in H₂O), as a white lyophilate in a yield of 1.02 g (87.8%).

TLC: $R_f$=0.31 (Silica gel; 20:1:1 CH₂Cl₂/CH₃OH/acetic acid)

¹NMR (270MHz; D₂O, Referenced with H₂O @4.65 ppm)

| δ | | |
|---|---|---|
| | 5.16 | (br s, 1H) |
| | 3.96–4.09 | (m, 1H) |
| | 3.68–3.83 | (m, 1H) |
| | 3.58–3.68 | (m, 1H) |
| | 2.18–2.37 | (ABX, 2H) |
| | 2.08–2.18 | (br d, 1H) |
| | 1.95 | (v br s, 1H) |
| | 1.80–1.90 | (br d, 1H) |
| | 1.00–1.60 | (m, 17H) |
| | 1.11 | (s, 3H) |
| | 1.10 | (s, 3H) |
| | 0.76–0.78 | (d, 3H, J=6.86Hz) |
| | 0.75–0.80 | (t, 2H, J=7.38Hz) |

Mass Spec: (FAB/SIMS) (M+Na)⁺ 4.65.
Elemental Analysis (%)
Calcd. for 1.0 moles H₂O
(Effective MW=482.60)

|   | Calc. | Found |
|---|-------|-------|
| C | 59.74 | 59.74 |
| H | 8.98  | 9.05  |

$[\alpha]_D = +45.0°$ (c=0.5, CH₃OH)

What is claimed is:

1. A compound of the structure

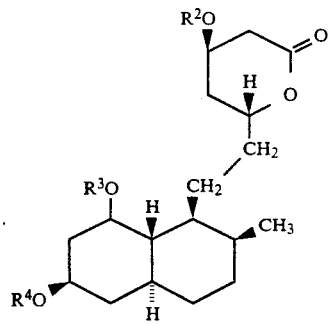

wherein R² is a silyl protecting group, R³ is H or

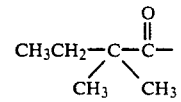

and R⁴ is a silyl protecting group.

2. The compound as defined in claim 1 wherein the silyl protecting group is tertiarybutyldimethylsilyl.

3. The compound as defined in claim 1 wherein R³ is H.

4. The compound as defined in claim 1 wherein R³ is

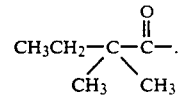

* * * * *